(12) United States Patent
Deshmukh et al.

(10) Patent No.: US 6,258,792 B1
(45) Date of Patent: Jul. 10, 2001

(54) CATIONIC CHOLESTERYL DERIVATIVES CONTAINING CYCLIC POLAR GROUPS

(75) Inventors: Hermant M. Deshmukh, Carlsbad, CA (US); Leaf Huang, Wexford, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/669,031

(22) Filed: Sep. 25, 2000

Related U.S. Application Data

(63) Continuation of application No. 08/858,166, filed as application No. PCT/US97/06066 on Apr. 11, 1997, now abandoned.

(51) Int. Cl.[7] ................................................. A01N 43/04

(52) U.S. Cl. ........................... 514/44; 540/108; 540/113; 540/107; 536/23.1; 514/231.2; 514/252.1

(58) Field of Search ..................................... 540/107, 108, 540/113; 536/23.1; 514/44, 231.2, 252.1

(56) References Cited

U.S. PATENT DOCUMENTS

| | | |
|---|---|---|
| 3,013,009 | 12/1961 | Marshall et al. . |
| 4,544,545 | 10/1985 | Ryan et al. . |
| 4,897,355 | 1/1990 | Eppstein et al. . |
| 4,958,013 | 9/1990 | Letsinger . |
| 5,100,662 | 3/1992 | Bolcsak et al. . |
| 5,283,185 | 2/1994 | Epand et al. . |
| 5,676,954 | 10/1997 | Brigman . |
| 5,756,353 | 5/1998 | Debs . |
| 5,795,587 | 8/1998 | Gao et al. . |
| 5,827,703 | 10/1998 | Debs et al. . |
| 5,877,302 | 3/1999 | Hanson et al. . |
| 6,008,202 | 12/1999 | Huang et al. . |
| 6,008,336 | 12/1999 | Hanson et al. . |
| 6,077,835 | 6/2000 | Hanson et al. . |

FOREIGN PATENT DOCUMENTS

| | | |
|---|---|---|
| WO 93/03709 A1 | 3/1993 | (WO) . |
| WO 93/05162 | 3/1993 | (WO) . |
| WO 95/25809 A1 | 2/1995 | (WO) . |
| WO 96/18372 | 6/1996 | (WO) . |
| WO 97/04748 | 2/1997 | (WO) . |
| WO 97/11682 A2 | 4/1997 | (WO) . |
| WO 97/11682 A3 | 4/1997 | (WO) . |
| WO 98/00110 A1 | 1/1998 | (WO) . |

OTHER PUBLICATIONS

Agocs, P. M. (1982). "Dealkylation side reaction in the synthesis of cholesteryl carbonates and carbamates," *Chemical Abstrats* 96(11):abstract No. 085843.

Allmann, R. et al. (1972). "Photochemical synthesis of 1,2–diazapines. VI. Molecular and crystal structure of 1,2–diazepines and their conformational mobility in solution," *Tetrahedron* 28(3):581–595.

Barrett, A. G. M. et al. (1981). "The deoxygentaion of N,N–dialkylaminothiocarbonyloxyalkanes," *Journal of the Chemical Society, Perkin Transactions 1* 5:1510–1515.

Capecchi, M. R. (1980). "High Efficiency Transformation by Direct Microinjection of DNA into Cutltured Mammalian Cells," *Cell* 22:479–488.

Cheetham, J. J. et al. (1990). "Cholesterol Sulfate Inhibits the Fusion of Sendai Virus to Biological and Model Membranes," *Journal of Biological Chemistry* 265:12404–12409.

Felgner, P.L. et al. (1987). *Proc. Natl. Acad. Sci.* 84:7413–7417.

Ferry, N. et al. (1991)."Retroviral–mediated Gene Transfer into Hepatocytes in vivo," *Proc. Natl. Acad. Sci.* 88:8377–8381.

Gagiu, F. et al. (1970). "New steroid compounds with possible antitumor action. II. N–(4R,5R'–thiazolyl–2__–cholesterylurethane," *Chemical Abstracts* 73(19):Abstract No. 099106.

Gagiu, F. et al. (1971). "New steroid compounds with potential anticancer activity. III. N–(1,3, 4–Thiadiazol–2–yl)cholesterylurethanes," *Annales Pharmaceutiques Francaises* 29(4)285–289.

Gao, X. et al. (1996). "Potentiation of Cationic Liposome–Mediated Gene Delivery by Polycations," *Biochemistry* 35:1027–1036.

Ishikawa, Y. et al. (1992). "High Efficiency Gene Transfer into Mammalian Cells by a Double Transfection Protocol," *Nucl. Acids Res.* 20:4367–4370.

Kunitake, T. et al. (1978). "Catalytic hydrolysis of phenyl esters in aqueous didodecyldimethylammonium vesicles: remarkable rate difference between intra– and intervervesicle reactions," *Journal of the American Chemical Society* 100(14):4615–4617.

Letsinger, R. L. et al. (1989)"Cholesteryl–Conjugated Oligonucleotides: Synthesis, Properties, and Activity as Inhibitors of Replication of Human Immunodefeciency Virus in Cell Culture," *Proc. Natl. Acad. Sci. USA* 86:6553–6556.

Leventis, R. et al. (1989). "Interactions of Mammalian Cells with Lipid Dispersions Containing Novel Metabloizable Cationic Amphiphiles," *Biochim. Biophys. Acta.* 1023:124–132.

Lichtenberg, D. et al. (1988) "Liposomes: Preparation, Characterization, and Preservation," *Meth. Biochem. Anal.* 33:337–462.

(List continued on next page.)

*Primary Examiner*—Barbara P. Badio
(74) *Attorney, Agent, or Firm*—Morrison & Foerster

(57) ABSTRACT

The present invention discloses compounds which are cationic cholesteryl derivatives having a nitrogen-containing ring structure as their polar head group. These compounds are useful for delivering biologically active substances to cells and for transfecting nucleic acids into cells.

41 Claims, 12 Drawing Sheets

OTHER PUBLICATIONS

Motoc, C. et al. (1979). "Mesomorphic properties of some sistosteryl esters," *Mol. Cryst. Liq. Cryst.* 53(1–2):69–76.

Okahata, Y. et al. (1979). "Catalytic hydrolysis of p–nitrophenyl esters in the presence of representative ammonium aggregates. Specific activation of a cholesteryl nucleophile bound to a dialkylammonium bilayer membrane," *Bulletin of the Chemical Society of Japan* 52(12):3674–3653.

Pacqereau, L. et al. (1992). "Electroporation–Mediated Gene Transfer into Hepatocytes: Preservation of a Growth Hormone Response," *Anal. Biochem.* 204:147–151.

Papanov, G. et al. (1989). "Synthesis of monochloroacetates and aminoesters of triterpenic acids and sterols," *Chemical Abstracts* 111(19):abstract No. 174521.

Pleurdeau, A. et al. (1982). "Synthesis of polymers with pharmacological properties. Introduction of peptide sequences into the macromolecular chain," *Chemical Abstracts* 96(9):abstract No. 069405.

Rose, J. K. et al. (1991). "A New Catatoic Liposome REagent Mediating Nearly Quantitative Transfection of Animal Cells," *BioTechniques* 10:520–525.

Solodin, I. et al. (1995). "A Novel Series of Amphiphilic Imidazolinium Compounds for In Vitro and In Vivo Gene Delivery," *Biochemistry* 34:13537–13544.

Stamatatos, L. et al. )1988). "Interactions of Catatonic Lipid Vesicles with Negatively Charged Phospholipid Vesicles and Biological Membranes," *Biochemistry* 27:3917–3925.

Wigler, M. et al. (1977). "Transfer of Purified Herpes Virus Thymidine Kinase Gene to Cultured Mouse Cells," *Cell* 11:223–232.

Wu, G. Y. et al. (1988). "Targeted Antagonism of Galactosamine Toxicity in Normal Rat Hepatocytes in Vitro," *J. Biol. Chem.* 263:4719–4723.

Yang, N. S. et al. (1990). "In vivo and in vitro Gene Transfer to Mammalian Somatic Cells by Particle Bombardment," *Proc. Natl. Acad. Sci. USA* 87:9568–9572.

Yoshikawa et al. (1995). "Diaminoalkanes with an Odd Number of Carbon Atoms Induce Compaction of a Single Double–Stranded DNA Chain," *FEBS Lett.* 361:277–281.

DC-CHOL (DC)

(Imidazol)propyl carbamoyl Cholesterol (IM)

(Pyridyl)ethyl carbamoyl Cholesterol (PY)

CATIONIC CHOLESTERYL DERIVATIVES CONTAINING CYCLIC POLAR GROUPS

CROSS-REFERENCE TO RELATED APPLICATIONS

This application is a continuation of U.S. patent application Ser. No. 08/858,166, filed Apr. 11, 1998, now abandoned, which is the U.S. National Phase of International Application PCT/US97/06066, filed on Apr. 11, 1997, which claims priority to U.S. patent application Ser. No. 08/631,203, which was filed Apr. 12, 1996, now abandoned.

FIELD OF THE INVENTION

This invention relates to cationic lipids and their use in delivering biologically active substances to cells. In particular, the invention relates to novel cationic cholesteryl derivatives containing cyclic polar groups and the use of these derivatives to deliver biologically active substances to ceils and to transfect nucleic acids into cells.

BACKGROUND OF THE INVENTION

The development of new forms of therapeutics which use macromolecules such as proteins or nucleic acids as therapeutic agents has created a need to develop new and effective means of delivering such macromolecules to their appropriate cellular targets. Therapeutics based on either the use of specific polypeptide growth factors or specific genes to replace or supplement absent or defective genes are examples of therapeutics which may require such new delivery systems. Clinical application of such therapies depends not only on efficacy of new delivery systems but also on their safety and on the ease with which the technologies underlying these systems can be adapted for large scale pharmaceutical production, storage, and distribution of the therapeutic formulations.

Gene therapy has become an increasingly important mode of treating various diseases. The potential for providing effective treatments, and even cures, has stimulated an intense effort to apply this technology to diseases for which there have been no effective treatments. Recent progress in this area has indicated that gene therapy may have a significant impact not only on the treatment of single gene disorders, but also on other more complex diseases such as cancer.

Success of a gene therapy protocol largely depends upon the vehicle used to deliver the gene. A variety of means exist to introduce a gene inside the cell including physical means such as microinjection (Capecchi, M. R. Cell (1980) 22:479–485), electroporation (Pacqereau, L. et al. *Anal. Biochem.* (1992) 204:147–151) and particle bombardment (Yang, N. -S. et al. *Proc. Natl. Acad. Sci. USA* (1990) 87:9568–9572)), biological means such as viruses (Ferry, N. et al. *Proc. Natl. Acad. Sci.* (1991) 88:8377–8381) and chemical means such as calcium phosphate (Wiegler, M. et al. *Cell* (1977) 11:223–232), DEAE dextran (Ishikawa, Y. et al. *Nucl. Acid Res.* (1992) 20:4367–4370), polylysine (Wu, G. Y. et al. *J. Biol. Chem.* (1988) 263:4429–4432) and cationic liposomes (Felgner, P. L. et al. *Proc. Natl. Acad. Sci.* (1987) 84:7413–7417)). Clinical application of such therapies depends not only on the efficacy of new delivery systems but also on their safety and on the ease with which the technologies underlying these systems can be adapted for large scale pharmaceutical production, storage, and distribution of the therapeutic formulations. Thus, an ideal vehicle for the delivery of exogenous genes into cells and tissues should be highly efficient in nucleic acid delivery, safe to use, easy to produce in large quantity and have sufficient stability to be practicable as a pharmaceutical.

Non-viral vehicles, which are represented mainly by cationic lipids, are one type of vehicle which have, for the following reasons, been considered for use in gene therapy. First, the plasmid DNA required for liposome-mediated gene therapy can be widely and routinely prepared on a large scale and is simpler and carries less risk than the use of viral vectors such as retroviruses. Second, cationic lipids are less toxic and less immunogenic than viral vectors and the DNA complexed with the lipids is better protected from degradation by nucleases. Third, liposome-mediated gene delivery, unlike retroviral-mediated gene delivery, can deliver either RNA or DNA. Thus, DNA, RNA or an oligonucleotide can be introduced directly into cells using cationic liposomes.

Among the numerous cationic amphiphiles which have been referred to as useful for transfecting nucleic acids into cells are cationic derivatives of cholesterol. For example, cholesterol (4'-trimethylammonio) butanoate (ChOTB) contains a trimethylammonium group connected to the 3'-hydroxyl group of cholesterol via a butanoyl spacer arm and cholesterol hemisuccinate choline ester (ChOSC) contains a choline moiety connected to the 3'-hydroxyl group via a succinyl spacer arm. However, the transfection activities of these amphiphiles are generally weak. (Leventis, R. et al. (1989) *Biochim. Biophys. Acta.*, 1023:124–132)

Epand et al. (U.S. Pat. No. 5,283,185) describe cationic derivatives of cholesterol in which primary, secondary, tertiary or quaternary alkyl ammonium groups are linked to cholesterol via the 3-hydroxy group. These cationic cholesterol derivatives, including 3β[N-(N', N'-dimethylaminoethane) carbamoyl] cholesterol (DC-Chol), are disclosed to be useful in transfecting nucleic acids into cells.

SUMMARY OF THE INVENTION

This invention relates to novel compounds having the formula:

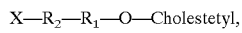

or salts thereof, where
$R_1$ is a linker bond

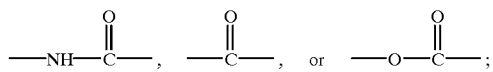

$R_2$ is a direct bond, a $C_1$–$C_{10}$ linear or branched chain alkylene or alkenylene group, a $C_3$–$C_7$ cyclokylene, preferably $C_5$–$C_6$, or a phenylene; and X is a 4–7-membered nitrogen-containing cyclic structure wherein said cyclic structure can optionally include further heteroatoms such as S, O or $NR_3$. The X-moiety can be linked to the $R_2$ spacer either via a carbon atom on the nitrogen-containing cyclic structure or via a nitrogen atom of the cyclic structure. $R_3$ mentioned hereinabove is H, $CH_3$, $C_2H_5$, $CH_2(CH_2)_z$ or $CH_2(CH_2)_z SH$ OH where z=0–3.

The invention further relates to lipid dispersions which comprise at least one compound of the present invention where by "lipid dispersions" as used throughout the specification and claims is meant liposomes, micelles, emulsions or lipoproteins.

The present invention also relates to biologically active substance: lipid complexes formed by mixing a biologically active substance with lipid dispersions comprising at least one compound of the invention. The invention further relates to biologically active substance:lipid:polycation complexes formed by mixing a biologically active substance with polycation and with lipid dispersions comprising at least one compound of the invention.

The invention therefore provides methods for delivering biologically active substances to cells where such methods may be utilized to deliver substances to cells in vitro or in vivo by contacting cells with the complexes of this invention.

The invention also provides a method of transfecting cells comprising (a) mixing nucleic acid which encodes a protein or peptide or, which effects gene expression, with lipid dispersions comprising at least one compound of the invention and optionally, polycation, to form nucleic acid:lipid or nucleic acid:lipid:polycation complexes and (b) contacting the cells with the complex. It is contemplated that the methods of transfection may be utilized in vitro or in vivo.

The invention flurther provides pharmaceutical compositions comprising at least one compound of the invention; pharmaceutical compositions comprising a lipid dispersion containing at least one compound of the invention; and pharmaceutical compositions comprising at least one complex of the invention.

The invention further relates to a kit containing a compound of the invention and/or a lipid dispersion containing at least one such compound. The invention also provides kits containing the complexes of the invention.

Lipid 2, 4{N-2-ethylamino [(3'-β-cholesteryl) carbamoyl]}piperazine;

Lipid 3, {N-2-ethylamino [(3'-β-cholesteryl) carbamoyl]}morpholine;

Lipid 4, {N-2-propylamino [(3'-β-cholesteryl) carbamoyl]}morpholine;

Lipid 5, N-methyl {4-N-amino [(3'-β-cholesteryl) carbamoyl]}piperazine;

Lipid 6, {N-2-ethylamino [(3'-β-cholesteryl) carbamoyl]}pyrrolidine; and

Lipid 7, {N-2-ethylamino [(3'-β-cholesteryl) carbamoyl]}piperidine.

Figure 3:
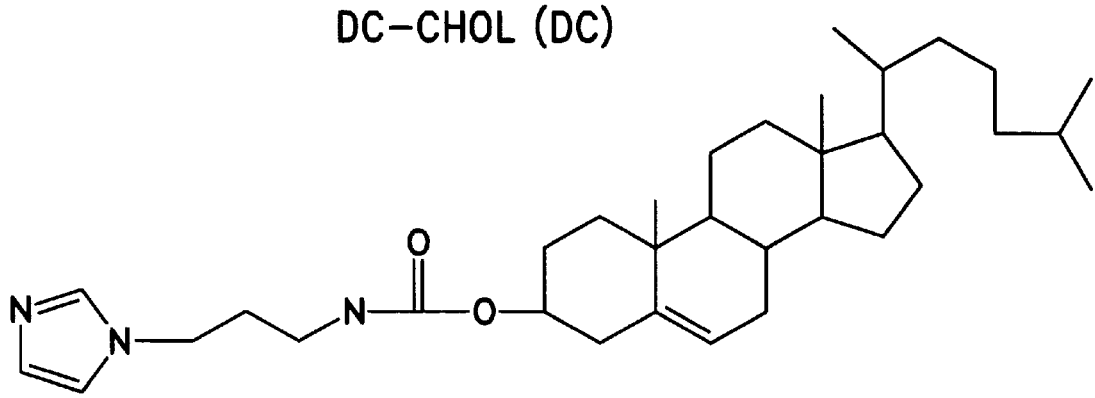
Figure 3:
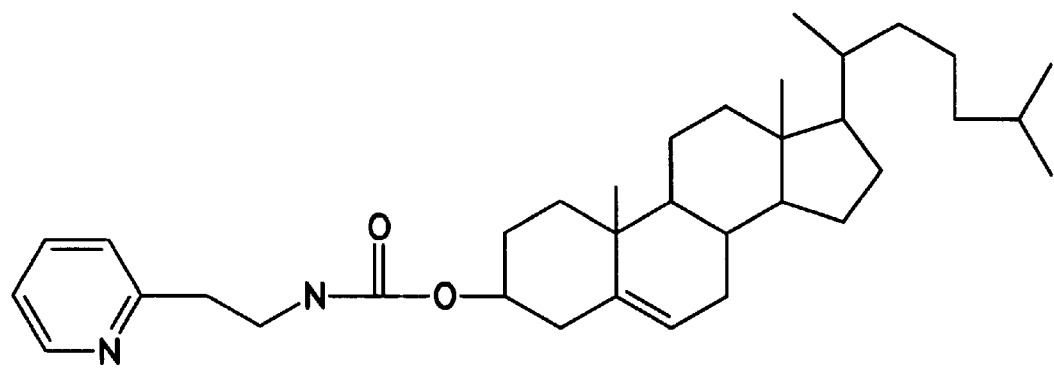

FIG. 3 shows structures of (imidazole) propyl carbamoyl cholesteryl (IM) and pyridyl (ethyl) carbamoyl cholesteryl (PY), two cholesterol derivatives which contain unsaturated nitrogen-containing rings.

Figure 4:
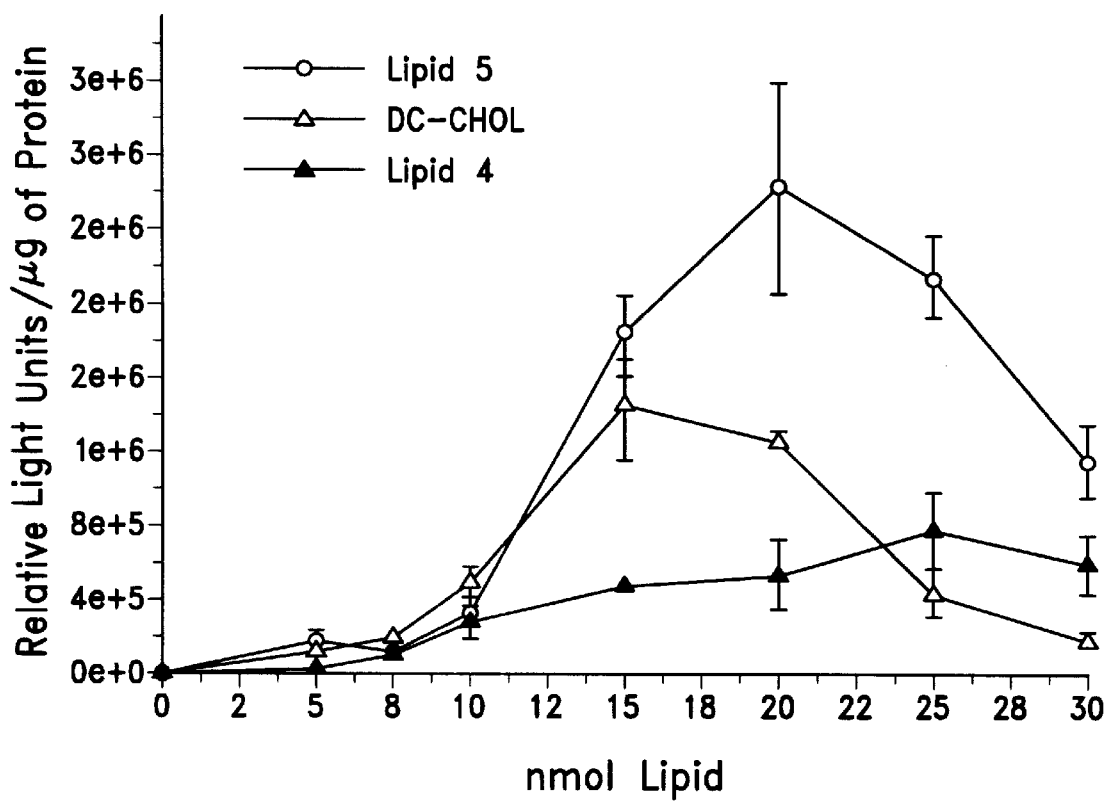

FIG. 4 shows luciferase activity in CHO cetls transfected with pCMV-Luc DNA complexed with varying nmol amounts of liposomes comprising DOPE and DC-Chol or DOPE and lipids 4 or 5 (mol:mol ratio of DOPE:cationic lipid of 1:1). Luciferase activity is indicated on the vertical axis of FIGS. 4–8 as relative light units (RLU)/μg protein and "nmol lipid" on the horizontal axis of FIGS. 4–8 refers to the total amount of liposomal lipid which is mixed with DNA to form the DNA lipid complexes which used to transfect the cells.

Figure 5:
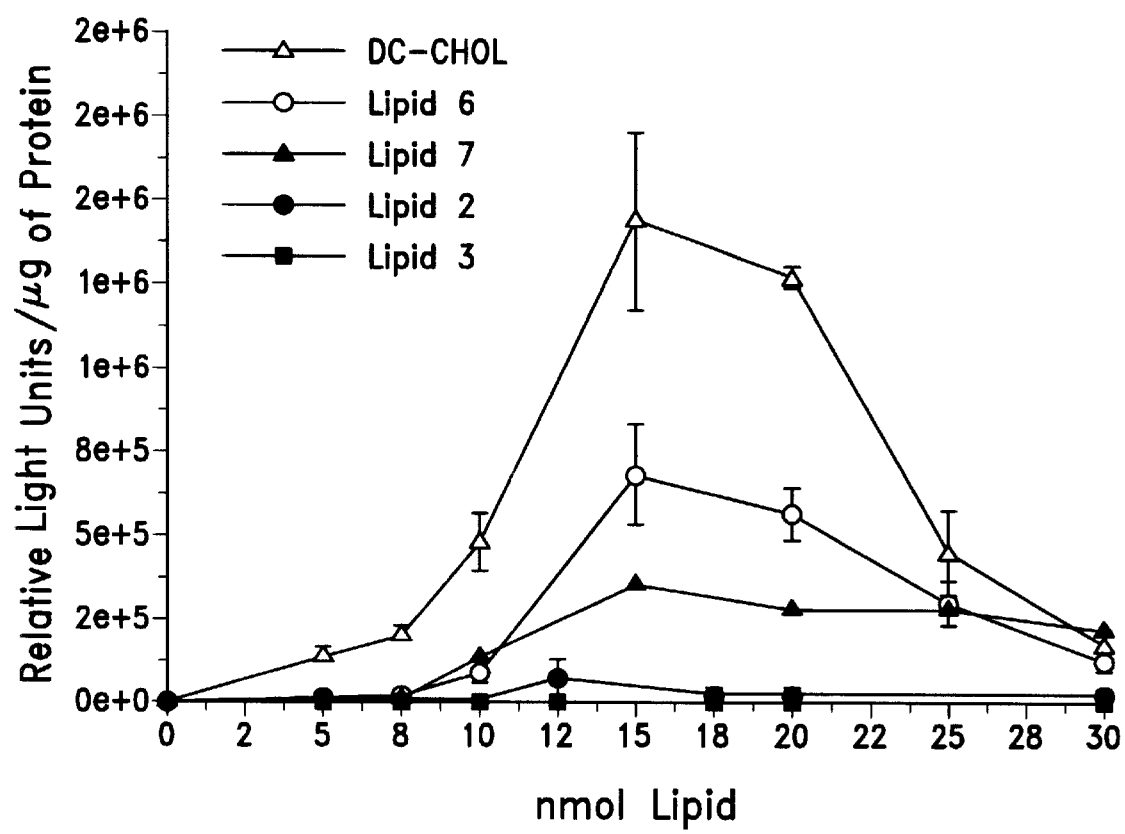

FIG. 5 shows luciferase activity in CHO cells transfected with pCMV-Luc DNA complexed with varying nmol amounts of liposomes comprising DOPE and DC-Chol or DOPE and lipids 2, 3, 6 or 7 (mol:mol ratio of DOPE:lipid of 1:1).

Figure 6:
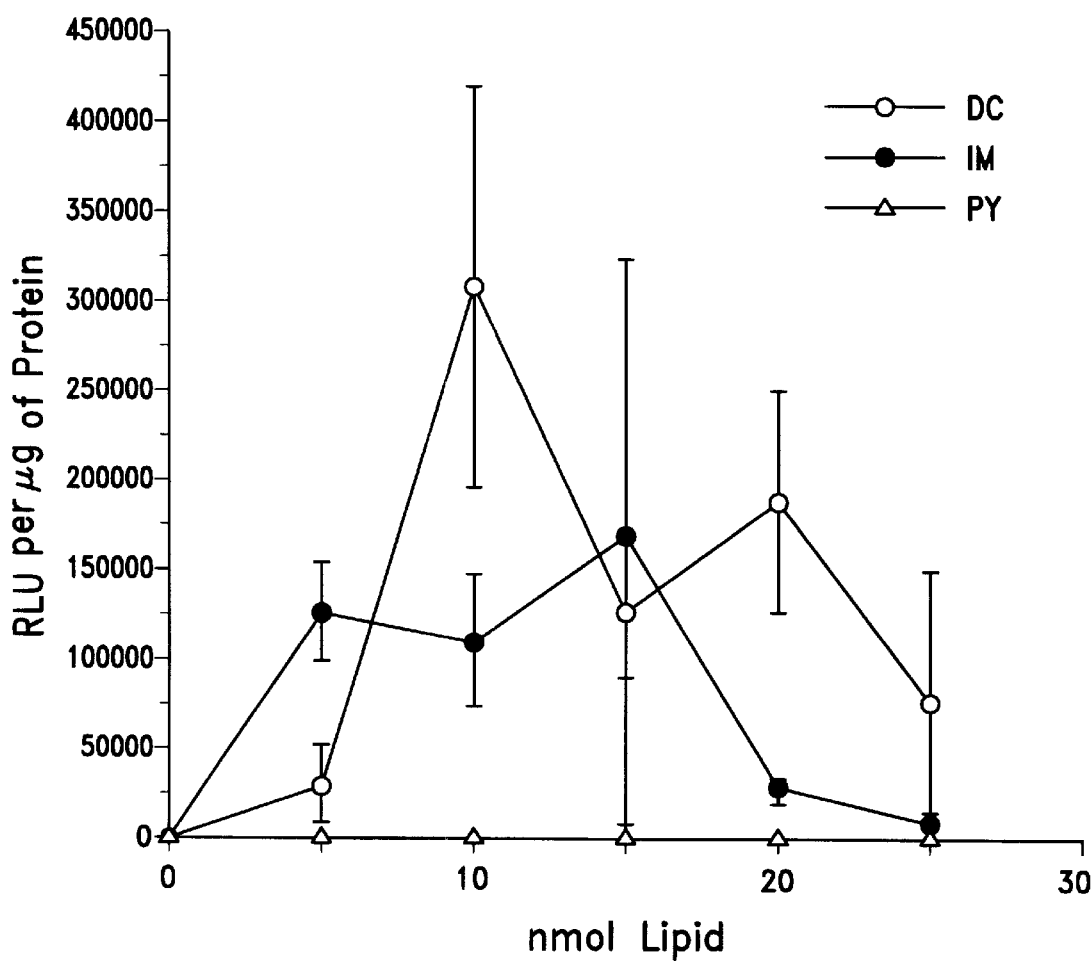

FIG. 6 shows luciferase activity in CHO cells transfected with pCMV-Luc DNA complexed with varying nmol amounts of liposomes comprising DC-Chol and DOPE or DOPE and (imidazole) propyl carbamoyl cholesteryl (IM) or DOPE and pyridyl (ethyl) carbamoyl cholesteryl (PY) (mol:mol ratio of DOPE:lipid of 1:1).

Figure 7:
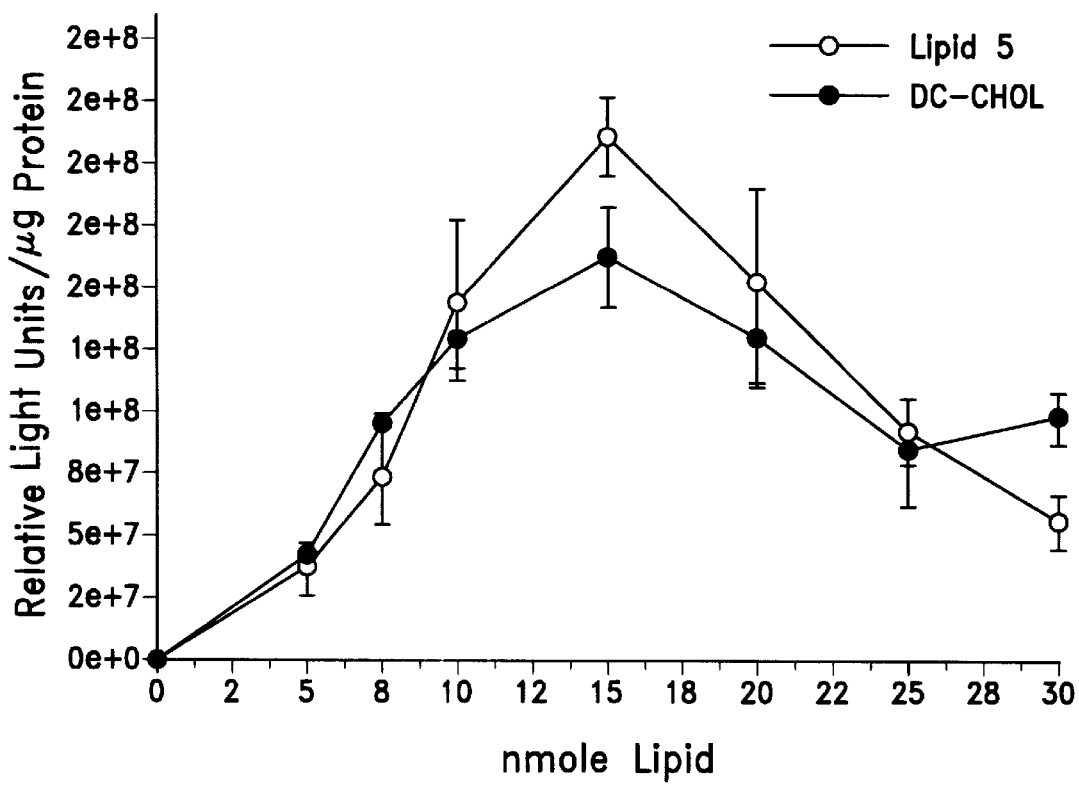

FIG. 7 shows luciferase activity in 293 cells transfected with pCMV-Luc DNA complexed with varying nmol amounts of liposomes comprising DOPE and DC-Chol or DOPE and lipid 5 in a mol:mol ratio of 1:1.

Figure 8:
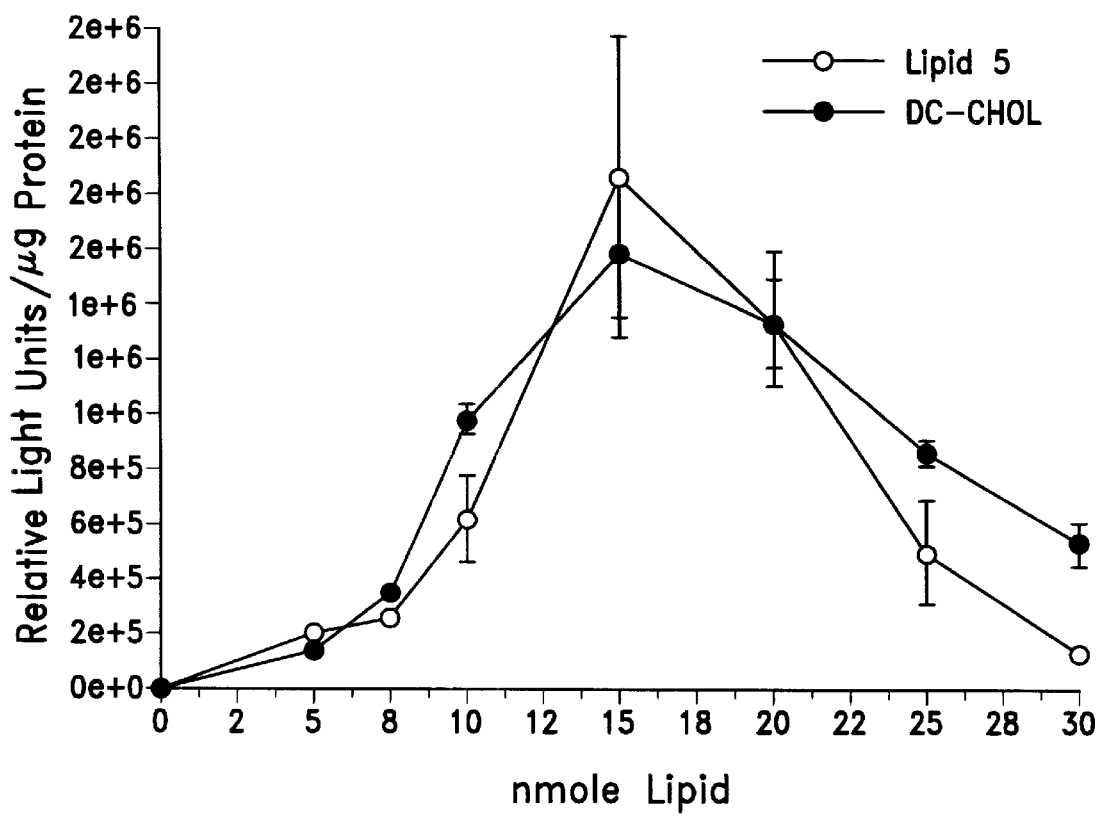

FIG. 8 shows luciferase activity in BL6 cells transfected with pCMV-Luc DNA complexed with varying nmol amounts of liposomes comprising DOPE and DC-Chol or DOPE and lipid 5 in a mol:mol ratio of 1:1.

Figure 9:
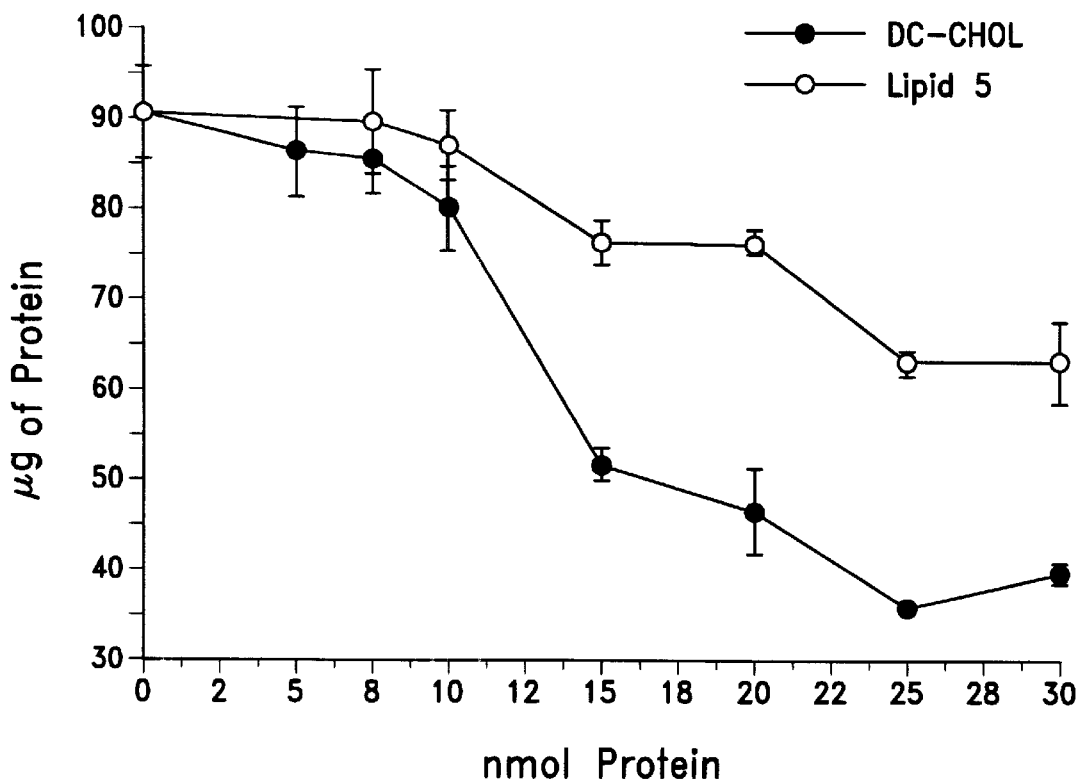

FIG. 9 shows the toxicity to CHO cells of varying nmol amounts of liposomes (indicated as mnol lipid on horizontal axis) comprising DOPE and lipid 5 or DOPE and DC-Chol in a mol: mol ratio of 1:1: Toxicity was assayed by measuring the amount of protein remaining in each well 36 hours after treatment with the indicated amount of liposome.

Figure 10:
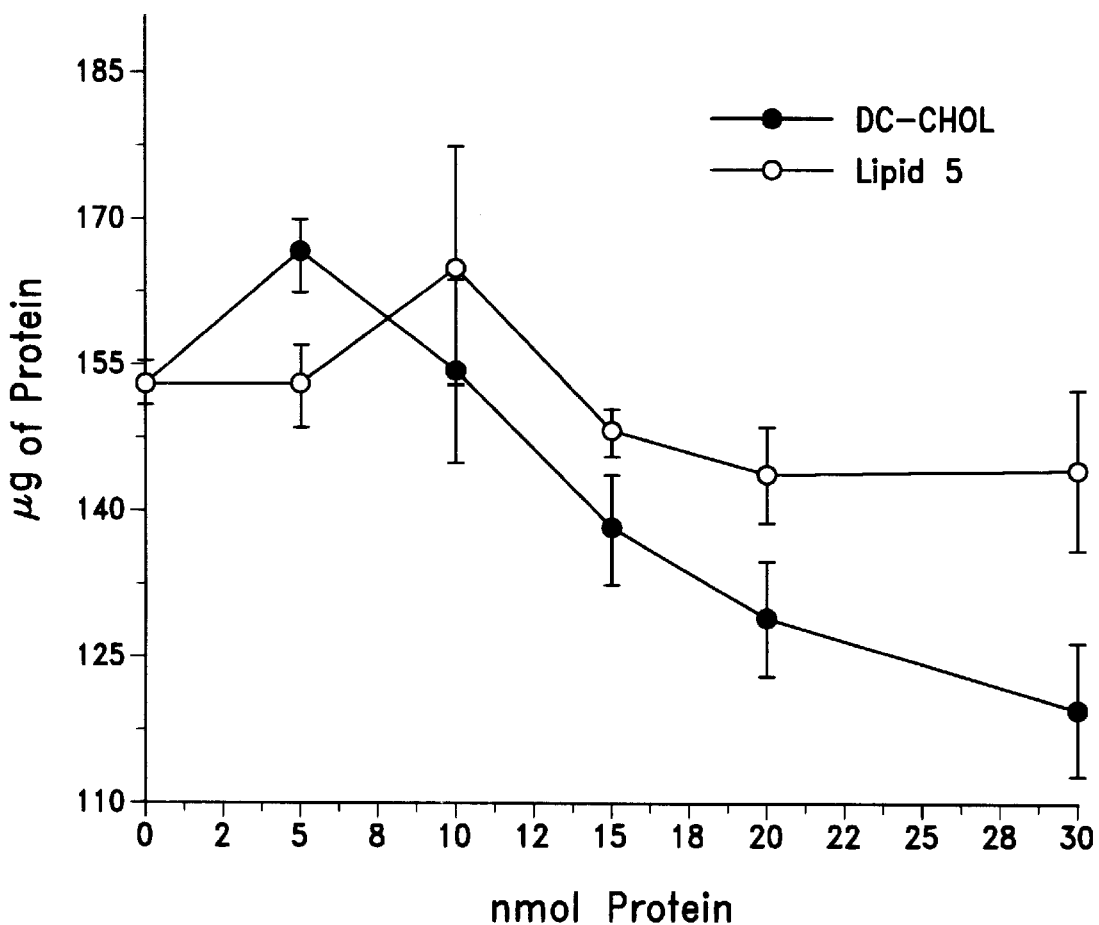

FIG. 10 shows the toxicity to BL6 cells of varying nmol amounts of liposomes (indicated as nmol lipid on horizontal axis) comprising DOPE and lipid S or DOPE and DC-Chol in a mol:mol ratio of 1:1. Toxicity was assayed by measuring the amount of protein remaining in each well 36 hours after treatment with the indicated amount of liposome.

Figure 11:
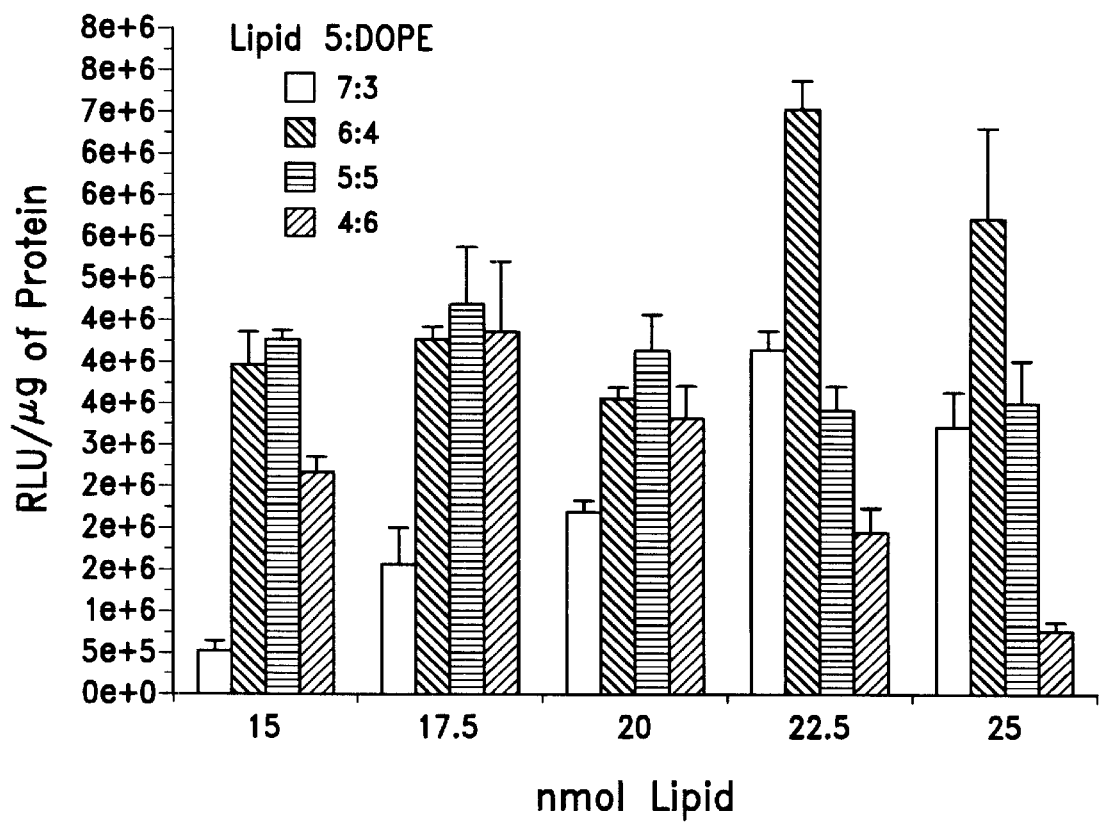

FIG. 11 shows the transfection activities of liposomes formulated with varying mol amounts of lipid 5 and DOPE (mol/mol). CHO cells were transfected with pCMV-Luc DNA complexed with varying nmol amounts of liposomes (horizontal axis) of the indicated lipid 5: DOPE mol/mol ratios and luciferase activity (vertical axis) was measured 36 hours after transfection with the DNA: lipid complexes.

Figure 12:
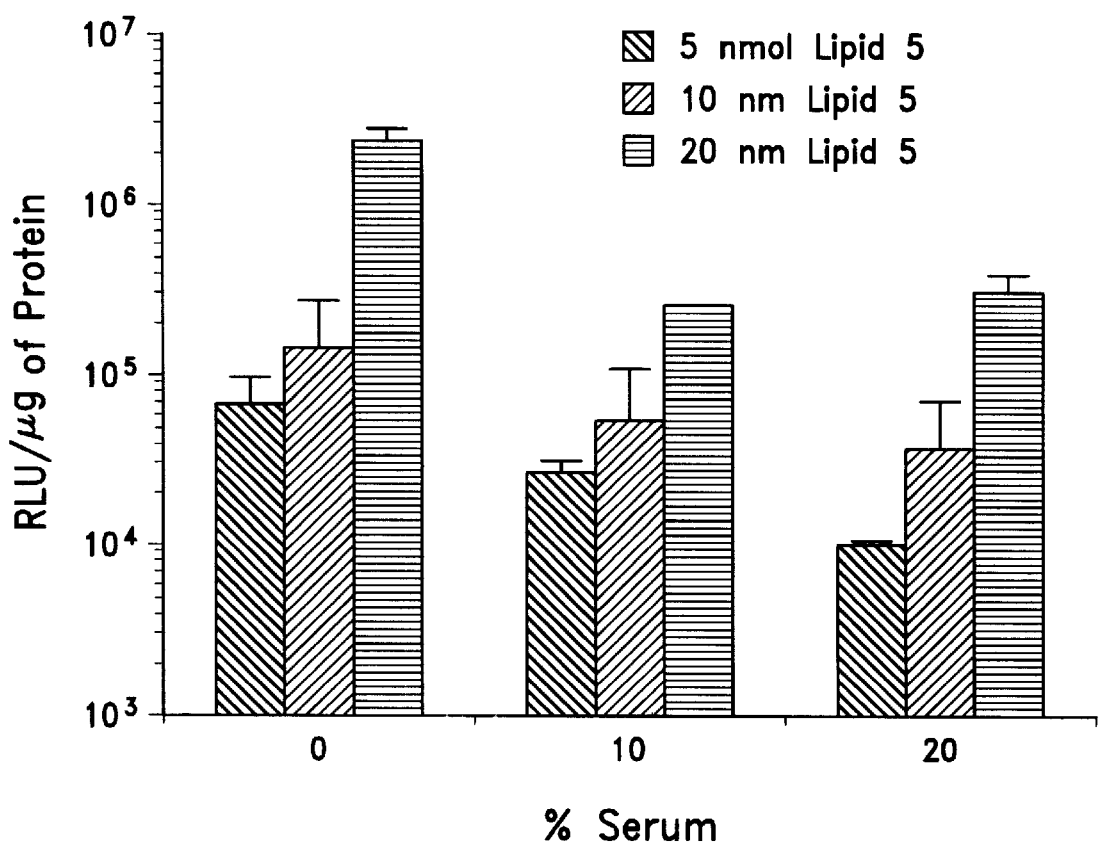

FIG. 12 shows luciferase activity in CHO cells transfected in the presence of 0, 10 or 20% fetal bovine serum with pCMV-Luc DNA (1 μg) complexed with 5, 10 or 20 nmol of lipid 5 in a 1:1 ratio with DOPE (mol/mol).

DESCRIPTION OF INVENTION

The present invention relates to compounds having the formula:

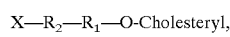
X—R$_2$—R$_1$—O-Cholesteryl, or salts thereof, where the oxygen is joined directly to the 3-carbon of the cholesteryl molecule; R$_1$ is

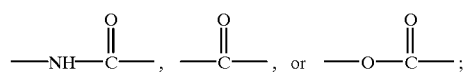

R$_2$ is a spacer arm and X is a nitrogen-containing cyclic structure.

In a preferred embodiment, R$_1$ is an

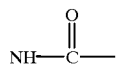

linker bond such that $R_1$—O— is

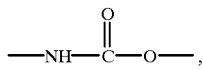

The $R_2$ spacer is a direct bond, a branched or linear alkylene or alkenylene chain of about 1 to about 10 carbon atoms in length, a $C_3$–$C_7$ cycloalkylene, preferably a $C_5$–$C_6$ cycloalkylene, or a phenylene. The branched chain alkylene and alkenylene structures have alkyl side groups which are generally, methyl, ethyl, propyl and isopropyl groups. The cyclic nitrogen—containing structure may be quaternized to form a polar head group. Variations in the length of the $R_2$ spacer may be made to place the positive charge of the polar head groups of the compounds in closer proximity to the negative charges of biologically active substances such as nucleic acids. In a preferred embodiment, $R_2$ is a linear alkylene group; in a more preferred embodiment, $R_2$ is a direct bond or a linear $C_1$–$C_3$ alkylene group and in a most preferred embodiment, $R_2$ is a direct bond.

X is a 4–7-membered nitrogen-containing cyclic structure wherein said cyclic structure can optionally include further heteroatoms such as S, O or $NR_3$. The X moiety can be linked to the $R_2$ spacer either via a carbon atom on the nitrogen—containing cyclic structure or via a nitrogen atom of the cyclic structure. $R_3$ mentioned hereinabove is —H, —$CH_3$, —$C_2H_5$, —$CH_2(CH_2)$,OH or —$CH_2(CH_2)_z$ SH where Z may be 0–3. The nitrogen-containing ring may be saturated or it may contain unsaturation provided that at least one nitrogen atom does not participate in a double bond and is available to possess a positive charge. In a preferred embodiment, X is a 4–6-membered saturated nitrogen-containing ring which optionally contains at least one additional O, S, or N heteroatom; in a more preferred embodiment, X is a 5–6-membered saturated nitrogen-containing ring which optionally contains at least one additional N, O, or S heteroatom; and in a most preferred embodiment, X is a six-membered saturated ring which optionally contains at least one additional heteroatom selected from the group consisting of N, S or O.

Preferred embodiments of the compounds of the invention include the following compounds:

1) X—$R_2$—$R_1$—O-Cholesteryl, where $R_1$ is

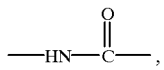

$R_2$ is a direct bond or a linear $C_1$–$C_3$ alkylene chain and X is a 4–6-membered nitrogen-containing cyclic structure which includes as a further heteroatom $NR_3$, where $R_3$ is as defined above.

2) X—$R_2$—$R_1$—O-Cholesteryl where $R_1$ is

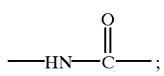

$R_2$ is a linear $C_1$–$C_3$ alkylene chain and X is a 4–6-membered nitrogen—containing cyclic structure which contains an O or an S as an additional heteroatom, 3) X—$R_2$—$R_1$—O-Cholesteryl where $R_1$ is

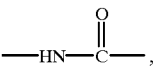

$R_2$ is a linear $C_1$–$C_3$ alkylene chain and X is a 4–6-membered nitrogen-containing cyclic structure which contains as an additional heteroatom $NR_3$, where $R_3$ is as defined above.

4) X—$R_2$—$R_1$—O-Cholesteryl where $R_1$ is

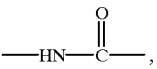

$R_2$ is a direct bond and X is a 5–7-membered nitrogen—containing cyclic structure which contains as an additional heteroatom $NR_3$, where $R_3$ is as defined above.

Figure 1:
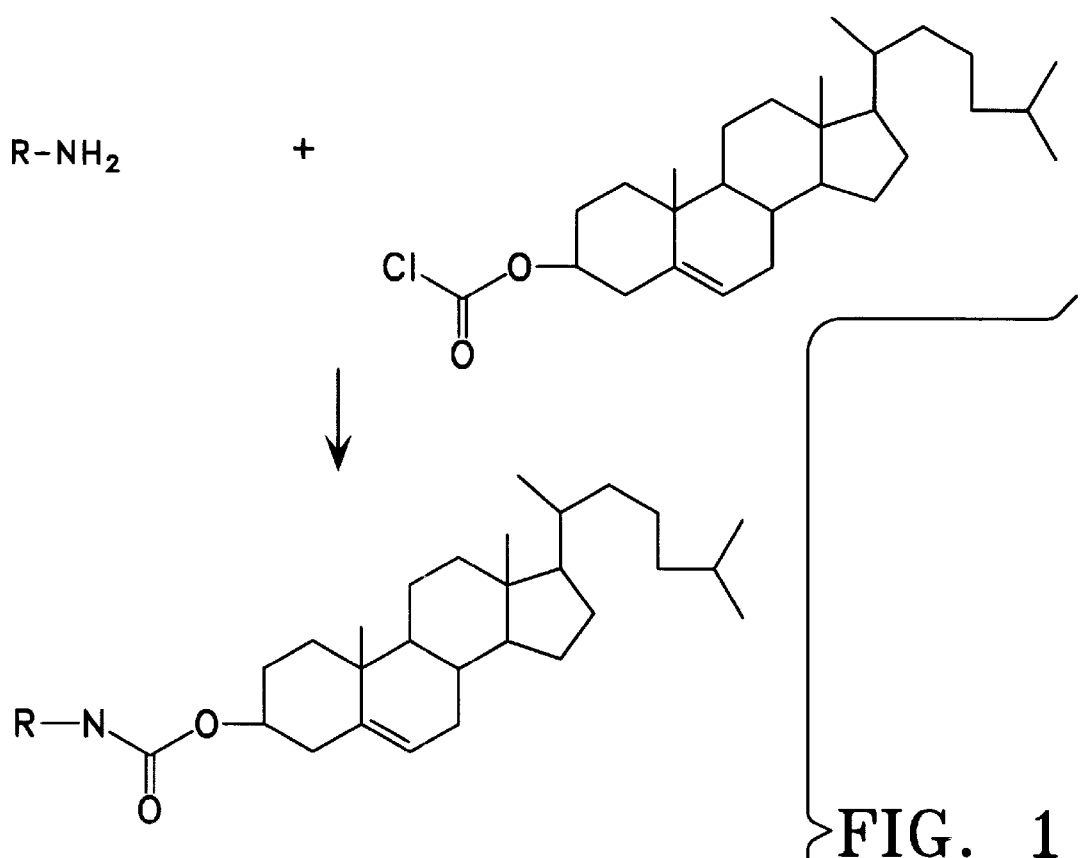
FIG. 1 shows the general route of synthesis for lipids 2–7, IM and PY.
Figure 2:
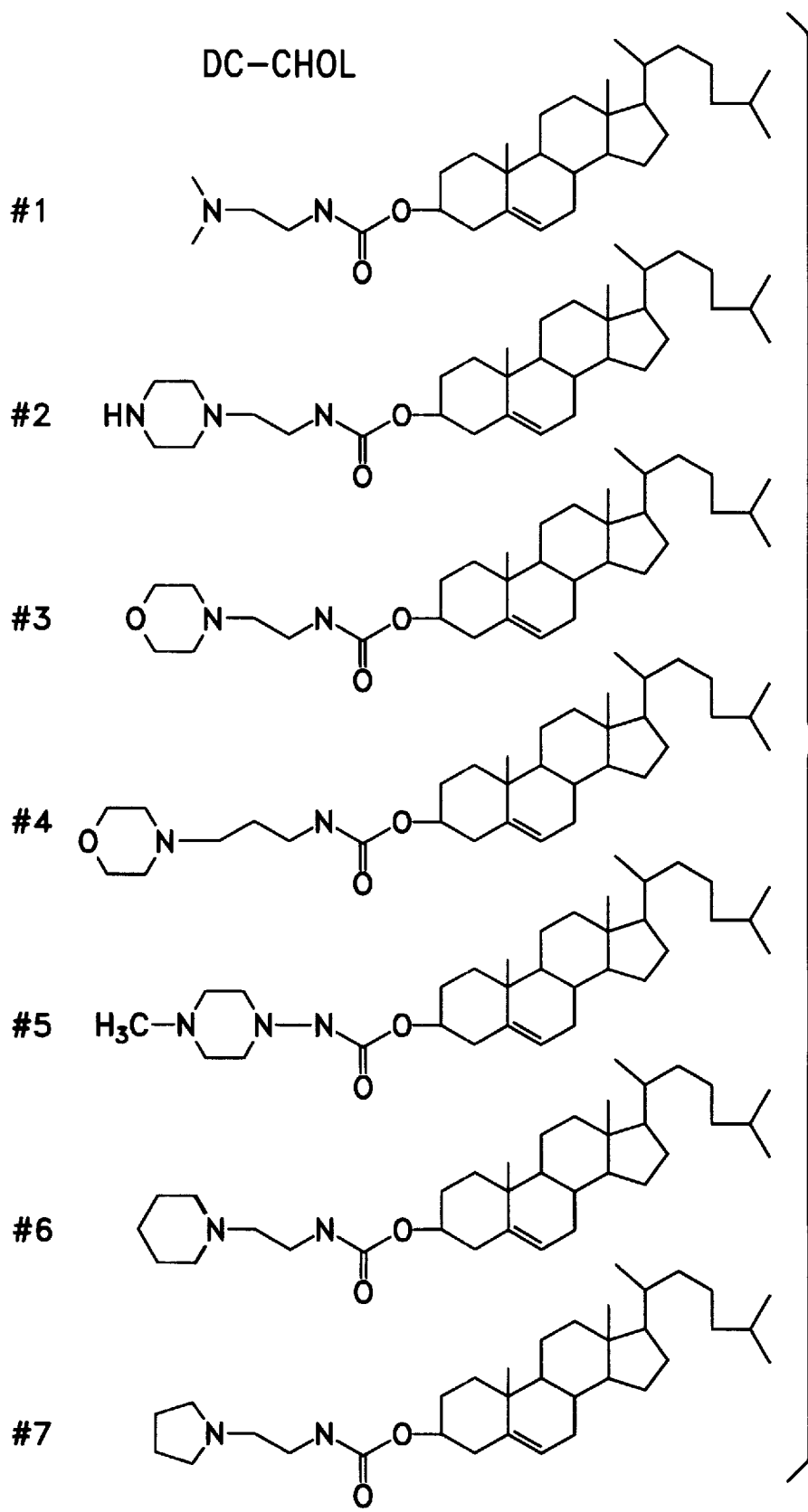
FIG. 2 shows the structures of lipids 2–7 synthesized by the route shown in FIG. 1.

In a more preferred embodiment, the compounds of the invention have the structures 4–7 shown in FIG. 2 and in a most preferred embodiment, the compound has structure 5 shown in FIG. 2.

The compounds of the present invention may be synthesized using standard reaction sequences known to those of ordinary skill in the art. In one embodiment, the compounds may be synthesized by attaching an X—$R_2$—$R_1$— molecule to O-cholesteryl. In an alternative embodiment, one may build from the O-cholesteryl molecule in a step-wise fashion to produce, for example, $R_1$—O-Cholesteryl, then $R_2$—$R_1$—O-Cholesteryl, and then X—$R_2$—$R_1$—O-Cholesteryl.

In yet another embodiment, the compounds of the invention may be synthesized by forming blocks of molecules and then coupling the blocks to each other to produce the desired compounds. Of course, regardless of the reaction sequence chosen to synthesize the compounds of the invention, those of ordinary skill in the art will readily understand that reactions for formation of the various functional group linkages contained in such compounds are well known in the art (Morrison and Boyd (1979) Organic Chemistry 3rd Edition, Allyn and Bacon, Inc., Boston, Mass.).

Once synthesized, the compounds of the invention may be used to formulate lipid dispersions such as liposomes, miceues, emulsions and lipoproteins by methods known to those of ordinary skill in the art. When used to formulate liposomes, for example, the compounds of the invention may be used in combination with other cationic lipids, neutral phospholipids or negatively charged lipids to form liposomes. Suitable cationic lipid species which may be combined with the compounds of the invention include, but are not limited to, 1,2 bis(oleoyloxy)-3-(trimethylammonio) propane (DOTAP); N-[1,-(2,3-dioleoyloxy) propyl]-N,N,N-trimethyl ammonium chloride (DOTMA) or other N-(N,N-1-dialkoxy)-alklyl-N,N,N-trisubstituted ammonium surfactants; 1,2 dioleoyl-3-(4'-trimethylammonio) butanoyl-sn-glycerol (DOBT) or cholesterol (4' trimethylammonia) butanoate (ChOTB) where the trimethylammonium group is connected via a butanoyl spacer arm to either the double chain (for DOTB) or cholesterol group (for ChOTB); DORI (DL-1,2-dioleoyl-3-dimethylaminopropyl-B-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesterol hemisuccinate ester (ChOSC); lipopolyamines such as doctadecylamidoglycylspermine (DOGS) and dipalmitoyl phosphatidyesthanolamidospermine (DPPES), or the cationic lipids disclosed in U.S. Pat. No. 5,283,185, cholesterol-3β-carboxylamido-ethylenetrimethylammonium iodide, 1-dimethylamino-3-trimethylammonio-DL-2-propyl-cholesterol carboxylate iodide, cholesterol-3β-carboxyamidoethyleneamine, cholesterol-3β-oxysuccinamido-ethylenetrimethylammonium iodide, 1-dimethylamino-3-trimethylammonio-DL-2-propyl-cholesterol-3β-oxysuccinate iodide, 2-[(2-trimethylammonio)-ethylmethylamino]ethyl-cholesterol-3β-oxysuccinate iodide, 3β[N-(N', N'-dimethylaminoethane) carbamoyl] cholesterol (DC-chol), and 3β-[N-(polyethyleneimine)-carbamoyl]-cholesterol.

Examples of preferred cationic lipids include cholesterol-3β-carboxyamidoethylenetrimethylammonium iodide, 1-dimethylamino-3-trimethylammonio-DL-2-propyl-cholesterol carboxylate iodide, cholesterol-3β-carboxyamidoethyleneamine, cholesterol-3β-oxysuccinamidoethylenetrimethylammonium iodide, 1dimethylamino-3-trimethylammonio-DL-2-propyl-cholesterol-3O-oxysuccinate iodide, 2-[(2-trimethylammonio)ethylmethylamino]ethyl-cholesterol-3β-oxysuccinateiodide, 3β[N-(N',N'-dimethyl-aminoethane)-carbamoyl]-cholesterol (DC-chol), and 3β[N-(polyethyleneimine)carbamoyl]-cholesterol.

In addition to cationic lipids, the liposomes may also contain other lipids. These lipids include, but are not limited to, lyso lipids of which lysophosphatidylcholine (1-oleoyllysophosphatidycholine) is an example, cholesterol, or neutral phospholipids including dioleoyl phosphatidyl ethanolamine (DOPE) or dioleoyl phosphatidylcholine (DOPC). The liposomes may also contain negatively charged lipids so long as the net charge of the complexes formed is positive. Negatively charged lipids of the invention are those comprising at least one lipid species having a net negative charge at or near physiological pH or combinations of these. Suitable negatively charged lipid species include, but are not limited to, phosphatidyl glycerol and phosphatidic acid or a similar phospholipid analog.

When a compound of the invention is to be combined with another lipid to formulate liposomes, a preferred lipid is a neutral phospholipid, most preferably DOPE. Preferred mol/mol ratios of compound of the invention:DOPE may range from about 3:7 to about 7:3.

It is to be understood that in considering lipids which may be combined with the compounds of the invention to produce liposomes, those of ordinary skill in the art are not restricted only to the use of the lipids recited above but rather, any lipid composition may be used so long as a cationic tiposome is produced.

Methods for producing such liposomes are known to those of ordinary skill in the art. A review of methodologies of liposome preparation may be found in *Liposome Technology* (CFC Press NY 1984); *Liposomes* by Ortro (Marcel Schher, 1987); *Methods Biochem Anol.* 33:337–462 (1988) and U.S. Pat. No. 5,283,185. Such methods include freeze-thaw extrusion and sonication. It is contemplated that both unilamellar liposomes (less than about 200 nm in average diameter) and multilamellar liposomes (greater than about 300 nm in average diameter) may be produced.

Once produced, the lipid dispersions of the invention may be mixed with biologically active substances to produce a biologically active substance:lipid complex.

In an alternative embodiment, lipid dispersions containing a compound of the invention may be mixed with polycation and a biologically active substance to form a lipid:polycation:biologically active substances complex. (Gao, X et al (1996) *Biochemistry* 35:1027–1036). Suitable polycations for use in forming such complexes are natural or synthetic amino acids, peptides, proteins, polyamines, carbohydrates and any synthetic cationic polymers. Nonlimiting examples of polycations include polyargie, polyornithine, protamines and polylysine, polybrene (hexadimethrine bromide), histone, cationic dendrimer, spermine, spermidine and synthetic polypeptides derived from SV40 large T antigen which has excess positive charges and represents a nuclear localization signal. A preferred polycation is poly-L-lysine (PLL).

By "biologically active substances" as used throughout the specification and claims is meant a molecule, compound, or composition, which, when present in an effective amount, reacts with and/or affects living cells and organisms. It is to be understood that depending on the nature of the active substance, the active substance may either be active at the cell surface or produce its activity, such as with DNA or RNA, after being introduced into the cell.

Examples of biologically active substances include, but are not limited to, nucleic acids such as DNA, cDNA, RNA (full length mRNA, ribozymes, antisense RNA, decoys), oligodeoxynucleotides (phosphodiesters, phosphothioates, phosphoramidites, and all other chemical modifications), oligonucleotide (phosphodiesters, etc.) or linear and closed circular plasmid DNA; carbohydrates; antibodies, proteins and peptides, including recombinant proteins such as for example cytokines (e.g. NGF, G-CSF, GM-CSF), enzymes, vaccines (e.g. HBsAg, gpl20); vitamins, prostaglandins, drugs such as local anesthetics (e.g. procaine), antimalarial agents (e.g. chloroquine), compounds which need to cross the blood-brain barrier such as anti-parkinson agents (e.g. leva-DOPA), adrenergic receptor antagonists (e.g. propanolol), anti-neoplastic agents (e.g. doxorubicin), antihistamines, biogenic amines (e.g. dopamine), antidepressants (e.g. desipramine), anticholinergics (e.g. atropine), antiarrhythmics (e.g. quinidine), antiemetics (e.g. chloroprimamine) and analgesics (e.g. codeine, morphine) or small molecular weight drugs such as cisplatin which enhance transfection activity, or prolong the life time of DNA in and outside the cells.

When the biologically active substances is an antigenic protein or peptide, the complexes formed by mixing the protein or peptide with lipid dispersions containing compound(s) of the present invention may be utilized as vaccines.

Preferred biologically active substances are negatively charged substances such as nucleic acids, negatively charged proteins and carbohydrates including polysaccharides, or negatively charged drugs.

The present invention therefore provides methods for delivering biologically active substances to cells. In one embodiment the method comprises:

(a) mixing a biologically active substance with a lipid dispersion containing at least one compound of the invention to form a biologically active substance:lipid complex; and (b) contacting the cells with the complexes. In an alternative embodiment, the method comprises:

(a) mixing a biologically active substance with lipid dispersions and a polycation to form a biologically active substance:lipid:polycation complex; and (b) contacting the cells with the complex.

It is contemplated that the methods of the invention may be used to deliver biologically active substances to cells in vitro or in vivo.

It is further understood that when the complexes of the invention are contacted with cells in vivo, the complexes may be used therapeutically and/or prophylactically depending on the biologically active substance contained in the complexes. The invention therefore provides for therapeutic and/or prophylactic formulations comprising the complexes of the invention where such formulations comprise the complexes in a physiologically compatible buffer such as, for example, phosphate buffered saline, isotonic saline or low ionic strength buffer such as 10% sucrose in $H_2O$ (pH 7.4–7.6) or in Hepes (pH 7–8, a more preferred pH being 7.4–7.6). The complexes may be administered as aerosols or as liquid solutions for intratumor, intravenous, intratracheal, intraperitoneal, and intramuscular administration. Those of ordinary skill in the art would readily understand that the actual amount of complex to be administered will depend upon the route of administration, the pharmaceutical properties of the individual treated, as well as the results desired.

The present invention also provides methods for transfecting nucleic acids into cells in vitro or in vivo. It is to be understood that when used to transfect cells in vivo the methods of transfection may be used for gene therapy. It is also contemplated that when used to formulate nucleic acid:lipid and nucleic acid:lipid polycation complexes useful for transfecting cells, the lipid dispersions can contain a compound of the invention or a compound having the formula:

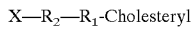

where $R_1$ is a direct bond to the 3 carbon of cholesteryl or a linker bond of the formulae

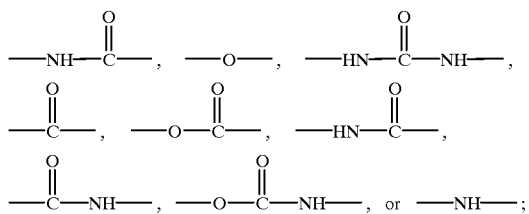

$R_2$ is a direct bond, a $C_1$–$C_{10}$ linear or branched chain alkylene or alkenylene group, a $C_3$–$C_7$ cycloalkylene, preferably $C_5$–$C_6$ cycloalkylene, or a phenylene, and X is a 4–7-membered nitrogen-containing cyclic structure wherein said cyclic structure can optionally include further heteroatoms such as S, O or $NR_3$. The X moiety can be linked to the $R_2$ spacer either via a carbon atom on the nitrogen-containing cyclic structure or via a nitrogen atom of the cyclic structure. $R_3$ mentioned hereinabove is H, $CH_3$, $C_2H_5$, $CH_2(CH_2)_z$ or $CH_2(CH_2)_zOH$ where z=0–3.

These compounds and the compounds of the invention preferably contain a saturated nitrogen-containing cyclic structure when used to form complexes for transfecting nucleic acids into cells In one embodiment, the method for transfecting nucleic acids into cells comprises:
(a) mixing nucleic acids with lipid dispersion and optionally polycation to form a nucleic acid:lipid or nucleic acid: lipid:polycation complex; and
(b) contacting cells with the complexes.

Nucleic acids to be transfected by the above method are nucleic acids which encode proteins or peptides or which regulate gene expression by effecting transcription and/or translation.

The ability of a compound to transfect nucleic acids into cells may be tested by contacting cells to complexes formed between a plasmid construct containing a reporter gene and lipid dispersions comprising at least one such compound. Such reporter genes are known to those of ordinary skill in the art and include, but are not limited to, the chloramphenicol acetyltransferase gene, the luciferase gene, the β-galactosidase gene and the human growth hormone gene. Cells which may be transfected by the complexes includes those cells which may be transfected by prior art lipid dispersions.

Any articles or patents referenced herein are hereby incorporated by reference. The following examples illustrate various aspects of the invention but are intended in no way to limit the scope thereof.

EXAMPLES

Materials and Methods
Synthesis of Cholesteryl Derivatives 2–7, IM and PY
In a 100 ml round-bottomed flask equipped with a stirrer and a dropping funnel, 1.1 mmol of reagent R—$NH_2$ and 0.05 ml triethylamine were dissolved in 15 ml dry chloroform. Cholesterol chloroformate (1 mmol) in 15 ml dry chloroform was added dropwise to the reagent solution with a constant stirring. The reaction was allowed to stir for 30 more minutes after the complete addition of cholesterol chloroformate. The thin layer chromatography (TLC) analysis of the reaction using silica gel TLC plates (7.5×2.5 cm) containing $F_{256}$ florescent indicator indicated that the reaction was complete. The solvent was evaporated to dryness and the solid residue was washed extensively with cold acetonitrile.

Purity of the product was judged by TLC analysis. When needed, further purification was performed on silica gel column using chloroform-methanol (75:25 vol/vol) as the eluent.

All the compounds were white amorphous powder. The yields for compounds 2–7, IM and PY varied between 74–85%.

Formulation of Liposomes
2 μmol of lipid dissolved in chloroform was transferred to a test tube. A solution of DOPE (2 umol) in chloroform was then added to this test tube. The chloroform was evaporated by passing a stream of nitrogen through the test tube to obtain a thin film of at the bottom of the test tube. Further drying was done in a desiccator under high vacuum for 30 minutes. 2 ml of distilled water was then added to the test tubes. The test tubes were stoppered and vortexed for one minute followed by sonication until the size of the particles was between 100 to 200 nm. The size of the particles was measured by Coulter particle size analyzer.

Cell Lines
CHO, 293 and BL6 cells were obtained from the American Type Culture Collection (ATCC). Chinese Hamster Ovarian ("CHO") cells were maintained in F-12 nutrient medium supplemented with 10% fetal bovine serum, antibiotics (1% penicllllin-streptomycin) and 1% glutamine; human embryonic kidney 293 cells and murine melanoma BL6 cells were cultured in DMEM medium supplemented with 10% fetal bovine serum, antibiotics (1% penicillin-streptomycin) and 1% glutamine.

Transfection Protocol
All the transfection experiments were performed in 48-well plates in the absence of serum except when specifically mentioned otherwise. Each well received DNA:lipid complex formed by mixing 1 μg of DNA (puc21 CMV luciferase or "pCMV-Luc") and various amounts of liposomes formulated from DOPE and the different cationic cholesterol derivatives (lipids 2–7, IM and PY). The DNA:lipid complexes were incubated with cells for 5 hours at 37° C. after which the cells were washed and resuspended in nutrient media (media+10% serum+antibiotic+1% glutamine). Cells were harvested 36 hours after transfection by lysis with 200 μL lysis buffer and aliquots of the lysate were assayed for luciferase activity and amount of protein.

Luciferase Activity Assay

Luciferase activity was assayed by measuring the luminescence obtained after adding the substrate (Promega) to in aliquot of lysate. This luminescence was measured in a luminometer for 25 seconds.

Assay for the Toxicity of Lipids

The toxicity of lipids was assayed by measuring the protein concentration in each well by Coomassie blue reagent (Pierce) 36 hours after transfection. Greater concentrations of protein per well indicated less toxicity of the tested lipids.

Example 1

Comparison of the Transfection Activities in CHO Cells of DNA:Lipid Complexes Formulated by Mixing DNA and Liposomes Containing DOPE and DC-Chol or DOPE and Lipids 2–7

FIGS. 4 and 5 show the luciferase activity in CHO cells of DNA:lipid complexes formulated using DC-Chol:DOPE liposomes or lipids 2, 3, 4, 5, 6 or 7. DOPE liposomes. The results presented in FIG. 4 show that the order of activity is lipid 5>DC-Chol>lipid 4; while FIG. 5 shows that lipids 6 and 7 are less active than DC-Chol and that lipids 2 and 3 have low activity. In sum, the results presented in FIGS. 4 and 5 suggest the following conclusions regarding the structure-activity relationship of lipids 2–7.

First, compounds having nitrogen in the ring can be equally or more active than those without ring nitrogens. The bulk of the ring does not interfere with the binding of the DNA. Condensation studies performed with these lipids and DNA corroborated this conclusion (data not shown). Second, the high activity of lipid 5 indicates that the spacer group between cholesterol and the charged head group can be very small. Third, the hydrogen bonding ability of oxygen does not produce any further enhancement in transfection activity. Fourth, the total lipid:DNA ratio for optimal activity varied slightly for different lipids. The differences in the apparent charge available for neutralization of DNA may be responsible for this difference.

In addition, the low activity of lipid 2 as shown in FIG. 5 was surprising since lipid 2 has a pyrazine ring and consequently it has two charges under physiological pH. Without being bound by theory, and without limiting the invention to even or odd numbered rings, one possible explanation for the low activity of lipid 2 could be the distance between the two nitrogens since it has been shown that distance between two nitrogens plays an important role in condensation of DNA. (Yoshikawa et al. (1995) FEBS Lett., 361:277–281). This publication reported that diaminoalkanes with odd number of carbon atoms compact the DNA whereas those with even number of carbon atoms do not. The low activity of lipid 3 in FIG. 5 is also surprising since lipid 4, which has only one carbon atom more than lipid 3, showed reasonable activity. The low activity of lipid 3 therefore appears to indicate that activity of the lipid might be sensitive to the spacer length.

Example 2

Comparison of Transfection Activity of DNA:Lipid Complexes Formulated by Mixing DNA and Liposomes Containing DOPE and either DC-Chol or Lipid IM or PY FIG. 6 shows that lipid IM is slightly less active than DC-Chol while lipid PY is much less active. It is believed that the low activity of lipid PY is because the only nitrogen in the pyridine ring is in a double bond and is therefore unavailable to possess a positive charge for interaction with the negatively charged DNA.

Example 3

Comparison of Transfection Activity of DNA:Lipid Complexes Formulated by Mixing DNA and Liposomes Containing DOPE and either Lipid 5 or DC-Chol Lipid 5 was further compared with DC-Chol by transfecting BL6 cells with lipid 5- or DC-Chol-containing DNA:lipid complexes (FIGS. 7 and 8 respectively). The results presented in FIGS. 7 and 8 show that lipid 5 is almost equally as active as DC-Chol in both 293 (FIG. 7) and BL6 (FIG. 8) cells. Lipid 5 was also tested in several cell lines including HeLa, Siha and Caski which are somewhat difficult to transfect when compared with CHO or 293 cells. In all these cell lines, lipid 5 was found to be slightly better than DC-Chol in its ability to transfect cells (data not shown). All the lipids showed absolute requirement of DOPE as the helper lipid and little or no activity was seen in the absence of DOPE (data not shown).

Example 4

Toxicity of Lipid 5 Relative to DC-Chol

FIGS. 9 and 10 show the toxicity of lipid 5 compared to that of DC-Chol in CHO and BL6 cells respectively, where toxicity was assessed by measuring the amount of protein in each well after transfection of cells with DNA:lipid complexes formulated by mixing DNA and liposomes containing DOPE and DC-Chol or DOPE and lipids. The results show that cells transfected with lipid 5-containing complex have more protein than cells transfected with DC-Chol-containing complex. In addition, when observed under microscope, the cells transfected with lipid 5-containing complex were healthy whereas those transfected with DC-Chol-containing complex showed some necrosis (data not shown). This reduced toxicity of lipid 5 relative to DC-Chol is the key feature of lipid 5. Of interest, lipids 2–4, 6 and 7 were also less toxic than DC-Chol while lipid PY exhibited comparable toxicity to DC-Chol and lipid IM was more toxic than DC-Chol.

Example 5

Optimization of Ratio between Lipid 5 and DOPE

FIG. 11 shows transfection activities of DNA: lipid complexes formulated using by mixing 1 μg of DNA and varying nmol amounts of liposomes containing different mol:mol ratios of lipid 5 and DOPE. The X axis of FIG. 11 refers to the total liposomal lipid mixed with 1 μg pCMV-Luc DNA: lipid complexes. All the ratios of lipid 5:DOPE shown formed stable liposomes (as measured by retention of diameter over time) but the complex formed from liposomes having a lipid 5:DOPE ratio of 6:4 showed the highest activity among all complexes while DNA:lipid complexes formed from liposomes having lipid 5:DOPE ratios of 5:5 and 4:6 had very similar transfection activities. Complexes formulated from liposomes having ratios outside these ratios (for example, lipid 5:DOPE ratios of 2:8 or 8:2) showed less activity indicating that liposomes containing roughly equal mol amounts of both lipid 5 and DOPE form more active complexes.

Example 6

Serum Sensitivity of Lipid 5

Serum sensitivity of lipid 5 was tested by adding fetal bovine serum to DNA: lipid complexes formed by mixing pCMV-Luc DNA and liposomes (1:1 lipid 5:DOPE) The serum concentrations were then adjusted to 10% or 20% of the final volume. The DNA:lipid complexes containing serum were then used to transfect CHO cells. Three different liposomal lipid:DNA ratios were chosen to observe the effect of the serum on the charge of the DNA:lipid complex. For example, at a ratio of 5 nmol lipids to 1 µg DNA, the complex has excess DNA and should be negatively charged. At 1 µg DNA: 10 nmol lipid 5, the DNA: lipid complex should be slightly positive and at 1 µg DNA:20 nmol lipid 5 the DNA:lipid complex has considerable amount of positive charge. FIG. 12 shows the results of these transfections where the data indicates that at lower ratios of lipid 5 to DNA the activity of the lipid S is affected by the serum to a lesser extent. For example, approximately 40% of the activity was retained relative to the activity of the 0% serum complexes when 5 and 10 nmol lipid 5 in the presence of 10% serum were used to transfect cells. However, when 20 nmol of lipid 5 in the presence of 10% serum was used to transfect cells, only 10% activity was retained indicating the sensitivity of the lipid to serum. DNA:lipid complexes formed from liposomes containing DOPE and either DC-Chol or DOTMA both showed similar serum sensitivity (data not shown)

Example 7

In Vivo Transfection using DNA:Lipid Complexes Formulated by Mixing pCMV-Luc DNA and Lipid 5: DOPE Liposomes Mice are injected intratumorally or intravenously with 50 µl of solution containing pCMV-Luc DNA (30 µg) complexed with 30 nmols of liposomal lipid (1:1 mol/mol lipid 5: DOPE). Animals are sacrificed 1–5 days later and extracts from tumor tissue (intratumor injection) or lung, liver and blood (intravenous injection) are assayed for luciferase activity and protein levels. The results show that DNA:lipid complexes containing lipid 5 exhibit in vivo transfection activity.

What is claimed is:

1. A nucleic acid:lipid complex for transfecting nucleic acids into cells, said complex comprising a nucleic acid and a compound having the structure:

X—$R_2$—$R_1$—O-Cholesteryl, wherein $R_1$ is a linker bond

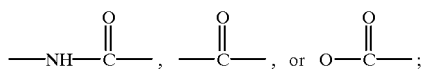

$R_2$ is a direct bond, a branched or linear alkylene or alkenylene chain of 1 to 10 carbons in length, a $C_3$–$C_7$ cycloalkylene, or a phenylene;

X is a 4–7-membered nitrogen-containing cyclic structure; and

X is linked to the $R_2$ spacer via a carbon atom of the nitrogen-containing cyclic structure or via a nitrogen atom of the cyclic structure.

2. The complex of claim 1, wherein $R_1$ is

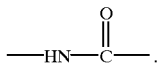

3. The complex of claim 2, wherein X is a saturated ring.
4. The complex of claim 3, wherein $R_2$ is a direct bond or a linear $C_1$–$C_3$ alkylene chain.
5. The complex of claim 4, wherein X is a 5–6-membered nitrogen-containing cyclic structure.
6. The complex of claim 5, wherein X further comprises a heteroatom selected from the group consisting of S, O, and $NR_3$, wherein $R_3$ is —H, —$CH_3$, —$C_2H_5$, —$CH_2(CH_2)_ZOH$ or —$CH_2(CH_2)_ZSH$, wherein Z is 0–3.
7. The complex of claim 6, wherein $R_2$ is a linear $C_2$ alkylene chain.
8. The complex of claim 5, wherein X is a 6-membered nitrogen-containing cyclic structure.
9. The complex of claim 8, wherein X further comprises a heteroatom selected from the group consisting of S, O, and $NR_3$, wherein $R_3$ is —H, —$CH_3$, —$C_2H_5$, —$CH_2(CH_2)_ZOH$ or —$CH_2(CH_2)_ZSH$, wherein Z is 0–3.
10. The complex of claim 9, wherein $R_2$ is a direct bond or is a linear $C_2$ alkylene chain.
11. The complex of claim 10, wherein $R_3$ is H and $R_2$ is a linear $C_2$ alkylene chain.
12. The complex of claim 10, wherein $R_2$ is a direct bond.
13. The complex of claim 12, wherein $R_3$ is a methyl group.
14. The complex of claim 8, wherein X is a 6-membered nitrogen-containiny cyclic structure which includes an additional heteroatom O.
15. The complex of claim 14, wherein $R_2$ is a linear $C_{1-3}$ alkylene chain.
16. The complex of claim 3, wherein X is an unsaturated ring.
17. The complex of claim wherein X is a 5–6-membered nitrogen-containing cyclic structure which can optionally include a further heteroatom.
18. The complex of claim 17, wherein $R_2$ is a direct bond or a linear $C_1$–$C_3$ alkylene chain.
19. The complex of claim 18, wherein X is a 5–6-membered nitrogen-containing cyclic structure which includes an additional heteroatom $NR_3$, wherein $R_3$ is —H, —$CH_3$, —$C_2H_5$, —$CH_2(CH_2)_ZOH$ or —$CH_2(CH_2)_ZSH$, wherein Z is 0–3.
20. The complex of claim 18, wherein X is a 5–6-membered nitrogen-containing cyclic structure linked to the $R_2$ spacer via a carbon atom on the nitrogen-containing cyclic structure.
21. The complex of claim 1, wherein $R_2$ is a $C_5$–$C_6$ cycloalkylene.
22. The complex of claim 1, wherein X comprises a further heteroatom.
23. The complex of claim 1, wherein X comprises a further heteroatom selected from the group consisting of S, O, and $NR_3$, where $R_3$ is —H, —$CH_3$, —$C_2H_5$, —$CH_2(CH_2)_ZOH$ or —$CH_2(CH_2)_ZSH$, wherein Z is 0–3.
24. The complex of claim 1, further comprising a polycation.
25. The complex of claim 24, wherein the cation is a polyamine.
26. The complex of claim 24, wherein the polycation is a poly-L-lysine.
27. The complex of claim 1, wherein the nucleic acid is selected from the group consisting of a DNA and an RNA molecule.

28. The complex of claim 1 wherein the nucleic acid encodes a protein or peptide or regulates gene expression by effecting transcription and/or translation.

29. A liposome comprising the complex of claim 1.

30. The complex of claim 1, further comprising a cationic lipid.

31. The complex of claim 30, wherein the cationic lipid is selected from the group consisting of cholesterol-3β-carboxyamidoethylenetrimethylammonium iodide, 1-dimethylamino-3-trimethylammonio-DL-2-propyl-cholesterol carboxylate iodide, cholesterol-3β-carboxyamidoethyleneamine, cholesterol-3β-oxysuccinamidoethylenetrimethylammonium iodide, 1-dimethylamino-3-trimethylammonio-DL-2-propyl-cholesterol-3β-oxysuccinate iodide, 2-[(2-trimethylammonio)ethylmethylamino]ethyl-cholesterol-3β-oxysuccinate iodide, 3β[N-(N',N'-dimethylaminoethane)-carbamoyl]-cholesterol(DC-chol), and 3β[N-(polyethyleneimine)-carbomoyl]cholesterol.

32. The complex of claim 1, further comprising a neutral lipid, a positively charged lipid or a negatively charged lipid.

33. The complex of claim 1, further comprising a lipid selected from the group consisting of cholesterol, dioleoyl phosphatidylethanolamine and dioleoyl phosphatidylcholine.

34. The complex of claim 1, wherein $R_1$

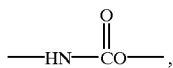

$R_2$ is a direct bond or a linear $C_1$–$C_3$ alkylene chain, and X is a 4–6-membered nitrogen-containing cyclic structure comprising a further nitrogen heteroatom.

35. The complex of claim 1, wherein $R_1$

$R_2$ is a linear $C_1$–$C_3$ alkylene chain, and X is a 4–6-membered nitrogen-containing cyclic structure comprising a further heteroatom selected from the group consisting of O, S, and N.

36. The complex of claim 1, wherein $R_1$

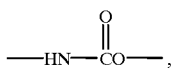

$R_2$ is a direct bond, and X is a 5–7-membered nitrogen-containing cyclic structure comprising a further nitrogen heteroatom.

37. The complex of claim 1, wherein the compound is

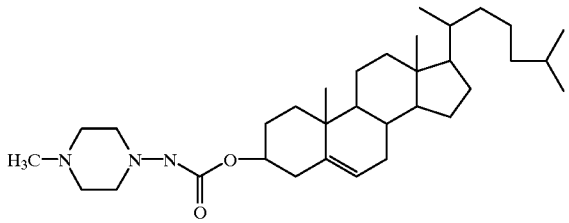

38. The complex of claim 34, 35 or 36, wherein X further comprises at least one additional heteroatom $NR_3$ where $R_3$ is —H, —$CH_3$, —$C_2H_5$, $CH_2(CH_2)_z$, —$CH_2(CH_2)_Z OH$ or —$CH_2(CH_2)_Z SH$, wherein Z is 0–3.

39. A lipid dispersion comprising a compound according to claim 11.

40. A pharmaceutical composition comprising at least one complex of claim 1.

41. A composition comprising the complex of claim 1 in a physiologically acceptable carrier.

* * * * *

UNITED STATES PATENT AND TRADEMARK OFFICE
CERTIFICATE OF CORRECTION

PATENT NO.    : 6,258,792 B1
DATED         : July 10, 2001
INVENTOR(S)   : Hemant M. Deshmukh and Leaf Huang It is certified that error appears in the above-identified patent and that said Letters Patent is hereby corrected as shown below:

Title page,
Item [75], Inventors, replace "Hermant" with -- Hemant --

Item [63], Related U.S. Application Data, please replace "Continuation of application No. 08/858,166, filed as application No. PCT/US97/06066, on Apr. 11, 1997, now abandoned." with
-- Continuation of application No. 08/858,166, filed April 11, 1997, which is the U.S. National Phase of application No. PCT/US97/06066, filed April 11, 1997, which claims priority to U.S. application No. 08/631,203, filed April 12, 1996. --

Item [56], OTHER PUBLICATIONS, The Kunitake reference title, replace "vervesicle" with -- vesicle reactions --

Column 14,
Line 30, replace "nitrogen-containiny" with -- nitrogen-containing --
Line 35, replace "claim 3" with -- claim 2 --
Line 37, add "16" after -- claim --

Column 16,
Lines 29 and 30, delete "$CH_2(CH_2)_Z$"
Line 32, replace "claim 11" with -- claim 1 --

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,258,792 B1
DATED         : July 10, 2001
INVENTOR(S)   : Hemant M. Deshmukh and Leaf Huang It is certified that error appears in the above-identified patent and that said Letters Patent is hereby corrected as shown below:

Title page,
Item [75], Inventors, replace "Hermant" with -- Hemant --
Item [63], Related U.S. Application Data, please replace "Continuation of application No. 08/858,166, filed as application No. PCT/US97/06066, on Apr. 11, 1997, now abandoned." with
-- Continuation of application No. 08/858,166, filed April 11, 1997, which is the U.S. National Phase of application No. PCT/US97/06066, filed April 11, 1997, which claims priority to U.S. application No. 08/631,203, filed April 12, 1996. --
Item [56], OTHER PUBLICATIONS, "The Kunitake" reference title, replace "vervesicle" with -- vesicle reactions --

Column 1,
Line 2, replace "1998" with -- 1997 --

Column 2,
Line 41, replace "cholestetyl" with -- cholesteryl --

Column 3,
Line 20, replace "flurthe" with -- further --
Line 53, replace "cetls" with -- cells --

Column 4,
Line 26, replace "lipid S" with -- lipid 5 --

Column 6,
Line 45, replace "miceues" with -- micelles --

Column 7,
Line 3, replace "carboxylamido-" with -- carboxyamido --
Line 12, replace "carbamoyl] cholseterol" with -- carbamoyl]-cholesterol --
Line 21, replace "1dimethylamino" with -- 1-dimethylamino --
Line 22, replace "cholesterol-30" with -- cholesterol $3\beta$ --
Line 24, replace "oxysuccinateiodide" with -- oxysuccinate iodide --
Line 24, replace "N'-dimethyl-aminoethane)" with -- N'-dimethylaminoethane) --

Column 8,
Line 6, replace "polyargie" with -- polyarginine --

Column 10,
Line 42, replace "thin film of at the bottom of the test tube" with -- thin film at the bottom of the test tube --
Line 54, replace "peniclllin" with -- penicillin --

UNITED STATES PATENT AND TRADEMARK OFFICE
CERTIFICATE OF CORRECTION

PATENT NO. : 6,258,792 B1
DATED : July 10, 2001
INVENTOR(S) : Hemant M. Deshmukh and Leaf Huang It is certified that error appears in the above-identified patent and that said Letters Patent is hereby corrected as shown below:

Column 13,
Line 20, replace "lipid S" with -- lipid 5 --

Column 14,
Line 30, replace "nitrogen-containiny" with -- nitrogen-containing --
Line 35, replace "claim 3" with -- claim 2 --
Line 37, add -- 16 -- after "claim"

Column 16,
Lines 29 and 30, delete "$CH_2(CH_2)_Z$"
Line 32, replace "claim 11" with -- claim 1 --

This certificate supersedes Certificate of Correction issued December 24, 2002.

Signed and Sealed this

Twenty-seventh Day of May, 2003

JAMES E. ROGAN
*Director of the United States Patent and Trademark Office*